United States Patent [19]

Pavlin

[11] Patent Number: 4,698,180

[45] Date of Patent: Oct. 6, 1987

[54] TERPENE ETHER AROMA CHEMICALS

[75] Inventor: Mark S. Pavlin, Lawrenceville, N.J.

[73] Assignee: Union Camp Corporation, Wayne, N.J.

[21] Appl. No.: 866,396

[22] Filed: May 23, 1986

[51] Int. Cl.$^4$ .......................... A61K 7/46; C11B 9/00; C07C 43/18

[52] U.S. Cl. ................................ 252/522 R; 568/665; 568/670; 568/672

[58] Field of Search .................... 252/522 R; 568/665, 568/668, 672, 602, 670

[56] References Cited

U.S. PATENT DOCUMENTS 4,354,043 10/1982 Belke et al. ......................... 568/665
4,443,633 4/1984 Boden et al. .................... 252/522 R
4,521,634 6/1985 Fujioka .......................... 252/522 R
4,544,775 10/1985 Fujioka .............................. 568/665
4,593,143 6/1986 Fujioka .............................. 568/665

OTHER PUBLICATIONS

Matsubara et al."Chemical Abstracts" vol. 83, (1975) p. 10428y.

Matsubara et al."Yukagku" vol. 24, No.3, (1975) pp. 28–29.

*Primary Examiner*—Werren B. Lone
*Attorney, Agent, or Firm*—Kane, Dalsimer, Kane, Sullivan and Kurucz

[57] ABSTRACT

A perfume composition comprises a perfumery carrier and isobornyl 2-hydroxypropyl ether.

2 Claims, No Drawings

TERPENE ETHER AROMA CHEMICALS

BACKGROUND OF THE INVENTION

Field of the Invention

The invention relates to fragrant compositions and more particularly relates to a fragrance composition which includes isobornyl 2-hydroxypropyl ether as an active ingredient.

BRIEF DESCRIPTION OF THE PRIOR ART

1-[(1,7,7-trimethylbicyclo[2.2.1]hept-2-yl)oxy]-propan-2-ol or isobornyl 2-hydroxypropyl ether (IBHPE) is a known compound as is the method of its preparation; see for example Matsubara et al., Synthesis of Terpenyl Hydroxyalkyl Ethers From Various Terpene Hydrocarbons And A Few Glycols, Yu Kagaku, Vol. 24, No. 3, pp. 28–29, 1975, which reported that the compound has a weak terpenyl ester-like fragrance, useful only as a retaining agent for fragrances.

The U.S. Pat. Nos. 4,443,633; 4,354,043; and 4,521,634 describe homologs or analogs of isobornyl 2-hydroxypropyl ether and their use in perfumery.

SUMMARY OF THE INVENTION

The invention comprises a perfume composition, which comprises; an effective amount for olfactory detection, of isobornyl 2-hydroxypropyl ether; and a perfumery acceptable carrier.

DETAILED DESCRIPTION OF THE PREFERRED EMBODIMENTS OF THE INVENTION

Isobornyl 2-hydroxypropyl ether, i.e.; the compound of formula:

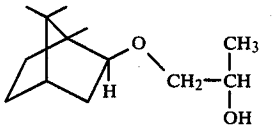

when added to and admixed with a conventional and perfumery acceptable carrier exhibits an unexpected woody tone. As such it is useful in perfumery.

In perfume compositions, it is the individual components which contribute their particular olfactory characteristics. However, the overall sensory effect of the perfume composition will be at least the sum total of the effects of each of the ingredients. Thus, the composition of matter prepared in accordance with the process of our invention can be used to alter, modify or enhance the aroma characteristic of a perfume composition, for example, by utilizing or moderating the olfactory reaction contributed by another ingredient or other ingredients in the composition.

The amount of isobornyl 2-hydroxypropyl ether used in accordance with the process of our invention is an olfactory detectable proportion. Such a proportion may be within the range of from about 0.001 to 50 percent by weight of the total perfumery composition. The amount will be effective in perfume compositions as well as in perfumed articles (e.g. perfumed polymers, anionic, nonionic, cationic or zwitterionic detergents, soaps, fabric softener compositions, fabric softener articles and hair preparations) and colognes.

Perfumery acceptable carriers are well known and are represented by a liquid, such as a non-toxic alcohol (e.g. ethyl alcohol), a non-toxic glycol (e.g. 1,2-propylene glycol) or the like. The carrier can also be an absorbent solid such as a gum (e.g. gum arabic or xanthan gum) or components for encapsulating the composition (such as a gelatin) as by coacervation or polymers such as urea formaldehyde polymers.

The compositions of the invention may be prepared by a simple, homogeneous admixture of the carrier and the active ingredient.

The following examples describe the manner and process of making and using the invetion and set forth the best mode contemplated by the inventor for carrying out the invention. All parts are by weight unless otherwise stated.

EXAMPLE 1

Two compositions are prepared by mixing the following ingredients:

| | (A) | CONTROL (B) |
|---|---|---|
| Lavandin Oil Grosso | 1.00 | 1.00 |
| Armoise Oil Tunis | 0.20 | 0.20 |
| Dimetol (IFF) | 0.60 | 0.60 |
| Bergamot Oil Bergapteneless | 0.60 | 0.60 |
| Patchouli Oil Indonesian Ironfree | 2.00 | 2.00 |
| Musk Ketone | 0.50 | 0.50 |
| Oakmoss Absolute Yugolavian 50% | 0.30 | 0.30 |
| Iso Butyl Quinolene | 0.05 | 0.05 |
| Amyl Salicylate | 0.30 | 0.30 |
| Coumarin | 0.35 | 0.35 |
| Geranium Oil Egyptian | 0.15 | 0.15 |
| Clove Bud Oil English | 0.20 | 0.20 |
| IBHPE | 4.00 | — |
| Dipropylene Glycol | — | 4.00 |
| | 10.25 | 10.25 |

The addition of isobornyl 2-hydroxypropyl ether (IBHPE) to this moder masculine Fougere accord extends the Patchouli character and impacts a rich woody vityvert theme in the composition (A), not found in the control (composition B).

EXAMPLE 2

Two components are prepared by mixing the following ingredients:

| | (A) | CONTROL (B) |
|---|---|---|
| Coumarin | 2.50 | 2.50 |
| Tonalid 2 | 1.00 | 1.00 |
| Galbanum Resinoid DS | 1.00 | 1.00 |
| Labdanum Resion Dark | 0.50 | 0.50 |
| Benzoin Sumatra Verarome | 1.00 | 1.00 |
| Iso Bornyl Acetate | 10.00 | 10.00 |
| Rosemary Oil Spanish | 7.50 | 7.50 |
| Agrumen Aldehyde Light | 1.50 | 1.50 |
| Lemon S.E.O. | 3.00 | 3.00 |
| Linalol Pure | 10.00 | 10.00 |
| Dihydro Myrcenol | 10.00 | 10.00 |
| Linalyl Acetate | 5.00 | 5.00 |
| Lavandin Oil Mixture | 10.00 | 10.00 |
| Lavender Oil Yugoslavia | 5.00 | 5.00 |
| Thymoxane | 1.50 | 1.50 |
| Dihydroisotagetone | 0.50 | 0.50 |
| Ginsene | 0.20 | 0.20 |
| Cedarwood Oil Chinese | 2.50 | 2.50 |
| Patchouli Oil Indonesian Ironfree | 1.50 | 1.50 |
| Osyrol | 2.50 | 2.50 |
| Geranium Oil | 2.50 | 2.50 |
| Aldehyde C10 | 0.50 | 0.50 |

-continued

| | (A) | CONTROL (B) |
|---|---|---|
| Aldehyde C12 (Lauric) | 0.50 | 0.50 |
| Aldehyde C12 (MNA) | 0.50 | 0.50 |
| Evernyl | 0.30 | 0.30 |
| Verdox | 5.00 | 5.00 |
| IBHPE | 7.50 | — |
| Para tert Butyl Cyclohyxyl Acetate | 6.50 | 6.50 |
| Dipropylene Glycol | — | 7.50 |
| | 100.00 | 100.00 |

IBHPE renders depth to fragrance, making it more long lasting and giving it more radiance and power as observed in the composition (A) and found lacking in the composition (B) a control.

EXAMPLE 3

Two compositions are made by mixing the following ingredients:

| | (A) | CONTROL (B) |
|---|---|---|
| Phenyl Ethyl Alcohol Extra | 27.00 | 27.00 |

-continued

| | (A) | CONTROL (B) |
|---|---|---|
| Linalol Pure | 10.00 | 10.00 |
| Benzyl Acetate | 14.00 | 14.00 |
| Lilestralis | 7.00 | 7.00 |
| Amyl Cinnamic Aldehyde | 7.00 | 7.00 |
| Alpha Terpineol UC | 10.00 | 10.00 |
| Gamma Methyl Ionone | 5.00 | 5.00 |
| Aldehyde C11 - Lenic | 0.50 | 0.50 |
| Coumarin Crystals | 3.00 | 3.00 |
| Terpinyl Acetate U.S.C | 1.50 | 1.50 |
| Para Tert Beutyl Cycloxyl Acetate | 10.00 | 10.00 |
| Diethyl Phthalate | 3.00 | 3.00 |
| IBHPE | 2.00 | — |
| Diethyl Phthalate | — | 2.00 |
| | 100.00 | 100.00 |

Isobornyl-2-hydroxypropyl ether adds a thickness to the above accord of composition (A) and enhances its woody, ambre characteristics. These advantages are not found in the control composition (B).

What is claimed is:

1. A perfume composition having a woody tone, which comprises; an effective amount for olfactory detection of the olfactory tone, of isobornyl 2-hydroxypropyl ether; and a perfumery acceptable carrier.

2. The composition of claim 1 wherein the carrier is selected from the group consisting of a non-toxic alcohol, a gum, a gelatin or a polymer.

* * * * *